United States Patent [19]
Fukushima et al.

[11] Patent Number: 6,117,948
[45] Date of Patent: Sep. 12, 2000

[54] PROCESS FOR PRODUCING ALIPHATIC AMINE DERIVATIVE

[75] Inventors: Tetsuaki Fukushima; Wataru Yoshida; Hiroshi Abe, all of Wakayama, Japan

[73] Assignee: Kao Corporation, Tokyo, Japan

[21] Appl. No.: 09/192,385

[22] Filed: Nov. 16, 1998

[30] Foreign Application Priority Data

Nov. 25, 1997 [JP] Japan ................... 9-323091

[51] Int. Cl.[7] ................. C08G 65/32; C08L 71/02
[52] U.S. Cl. ................. 525/409; 564/497; 564/505
[58] Field of Search ................. 528/405; 564/497, 564/505; 525/409

[56] References Cited

U.S. PATENT DOCUMENTS

| | | |
|---|---|---|
| 2,422,503 | 6/1947 | Smith . |
| 3,207,790 | 9/1965 | Glew et al. . |
| 3,585,239 | 6/1971 | Stein et al. ............. 564/497 |
| 5,019,653 | 5/1991 | Speranza et al. ............. 564/497 |

FOREIGN PATENT DOCUMENTS 54-24807  2/1979  Japan .

Primary Examiner—Robert Dawson
Assistant Examiner—D. Aylward
Attorney, Agent, or Firm—Oblon, Spivak, McClelland, Maier & Neustadt, P.C.

[57] ABSTRACT

The present invention provides a process for easily producing an alkylene oxide adduct to an aliphatic amine compound which has a fully excellent color, is not turbid, and does not deteriorate in color even through long-term storage. That is, the present invention provides a process for producing an alkylene oxide adduct to a primary or secondary amine compound having an aliphatic, saturated or unsaturated, hydrocarbon radical having 8 to 22 carbon atoms, having an excellent color, by reacting an alkyene oxide to the amine compound, characterized by comprising the step of adding a base or an aqueous solution thereof to the amine compound and then heating the mixture.

6 Claims, No Drawings

PROCESS FOR PRODUCING ALIPHATIC AMINE DERIVATIVE

TECHNICAL FIELD

This invention relates to a process for producing an aliphatic amine derivative. More particularly, it relates to a process for producing an alkylene oxide adduct to an aliphatic amine which has an excellent color, is not turbid, and can retain the excellent color even after long-term storage.

BACKGROUND ART

Alkylene oxide adducts of aliphatic amine compounds are important compounds in the field of products for household and industrial uses. In particular, they are used as starting materials for surfactants, intermediates for fiber treatments and for bactericidal substances, and components of insecticides and of fiber softeners. In these applications, the adducts desirably are pure and colorless substances.

Such alkylene oxide adducts of aliphatic amine compounds are obtained from aliphatic amine compounds, as starting materials, derived from animal fats such as beef tallow, vegetable oils such as coconut oil and palm oil, and the like by causing these aliphatic amine compounds to add an alkylene oxide. However, the alkylene oxide adducts obtained from such aliphatic amines derived from animal fats, vegetable oils, and the like have problems, for example, that generally they are colored or are turbid and they deteriorate in color through long-term storage to give products which are poor in appearance.

Since such colored or turbid alkylene oxide adducts arouse troubles when used in such applications as the aforementioned ones, methods for obtaining alkylene oxide adducts having an excellent color have conventionally been proposed. For example, a method in which an acid treatment is conducted when an alkylene oxide is added to an aliphatic amine (specification of U.S. Pat. No. 2,422,503), a method in which an alkali metal salt of boron hydride is added (specification of U.S. Pat. No. 3,207,790), and a method in which a reaction is conducted at a low temperature (JP-B 51-40052 corresponding to U.S. Pat. No. 3,585,239) are disclosed. Other techniques which have been disclosed include a method in which an alkylene oxide is added to an aliphatic amine and the resultant adduct is aged at 180 to 280° C. for 1 to 20 hours (JP-A 54-24807).

However, these methods have drawbacks, for example, that the operation is complicated or a fully excellent color and transparency cannot be obtained.

SUMMARY OF THE INVENTION

Accordingly, an object of this invention is to provide a process for easily producing an alkylene oxide adduct of an aliphatic amine compound which has a fully excellent color, is not turbid, and does not deteriorate in excellent color even through long-term storage.

This invention provides a process for producing an alkylene oxide adduct of a primary or secondary amine compound having an aliphatic, saturated or unsaturated, hydrocarbon radical having 8 to 22 carbon atoms, having an excellent color, by reacting an alkylene oxide to the amine compound, characterized by comprising the step of adding a base or an aqueous solution thereof to the amine compound and then heating the mixture.

DETAILED DESCRIPTION OF THE INVENTION

Examples of the amine compound having an aliphatic, saturated or unsaturated, hydrocarbon radicals each having 8 to 22 carbon atoms for use in this invention include octylamine, decylamine, laurylamine, stearylamine, behenylamine, oleylamine, dioctylamine, dilaurylamine, distearylamine, and laurylstearylamine.

These compounds may be used alone or in combination of two or more thereof. Aliphatic amines derived from animal fats such as beef tallow, vegetable oils such as coconut oil and palm oil, and the like may also be used.

This invention is characterized in that the primary or secondary amine compound having an aliphatic, saturated or unsaturated, hydrocarbon radicals each having 8 to 22 carbon atoms is one obtained through addition of a base or an aqueous solution thereof and treatment with the same with heating. The term "base" used in this invention means not only a base in a narrow sense which is alkaline in aqueous solutions but one in a wide sense which is defined as a proton acceptor by Brønsted et al. Preferred examples of the base for use in this invention include alkali metals and alkaline earth metals of hydroxides, carbonates, hydrogen carbonates, phosphates, hydrogen phosphates, and dihydrogen phosphates. Specific examples thereof include lithium hydroxide, sodium hydroxide, potassium hydroxide, cesium hydroxide, sodium carbonate, potassium carbonate, cesium carbonate, sodium hydrogen carbonate, potassium hydrogen carbonate, sodium phosphate, potassium phosphate, sodium hydrogen phosphate, potassium hydrogen phosphate, sodium dihydrogen phosphate, and potassium dihydrogen phosphate. More preferred among these bases are lithium hydroxide, sodium hydroxide, potassium hydroxide, sodium hydrogen carbonate, potassium hydrogen carbonate, sodium phosphate, potassium phosphate, sodium hydrogen phosphate, potassium hydrogen phosphate, sodium dihydrogen phosphate, and potassium dihydrogen phosphate, and most preferred among these bases are sodium hydroxide, potassium hydroxide, and sodium or potassium of hydrogen phosphate and dihydrogen phosphate.

These bases may be added in any form of, e.g., a powder or aqueous solution. The addition amount of these bases or their aqueous solutions is desirably 0.05 to 5% by weight, preferably 0.1 to 2.0% by weight in terms of pure base amount based on the primary or secondary aliphatic amine.

The treatment with the base or its aqueous solution with heating in this invention is desirably conducted at ordinary or reduced pressure and at 60 to 180° C. with mixing/stirring for 0.1 to 3 hours. The treatment is preferably conducted at 80 to 160° C. with mixing/stirring for 1 to 2 hours. The stirring may be conducted in any of air and an inert gas atmosphere.

After the treatment with heating in this invention, the amine is preferably separated from the mixture by filtering and/or distilling it.

Although the separation of the aliphatic amine after the treatment with a base or an aqueous solution thereof with heating can be conducted by the distillative separation method, centrifugal filtration method, etc., it is preferred to use the distillative separative method.

Subsequently, the primary or secondary amine compound having an aliphatic, saturated or unsaturated, hydrocarbon radicals each having 8 to 22 carbon atoms which has been thus treated with a base or an aqueous solution thereof is caused to add an alkylene oxide.

Examples of the alkylene oxide for use in this invention include ethylene oxide, propylene oxide, and butylene oxide. Preferred are ethylene oxide and propylene oxide. Ethylene oxide is especially preferred. The number of moles of the added alkylene oxide is preferably 1 to 30 per mole of the primary or secondary aliphatic amine compound.

The conditions for the alkylene oxide addition reaction in this invention are not particularly limited. Although ordinary alkylene oxide addition reaction conditions can be used, the reaction is preferably conducted at a temperature of 120 to 180° C.

By using the aliphatic amine thus obtained through the treatment with a base or an aqueous solution thereof, an alkylene oxide adduct having an excellent color can be obtained even when the alkylene oxide addition-reaction is conducted at high temperatures. This addition reaction necessitates neither the addition of a treatment such as an acid or an alkali metal salt of boron hydride nor an operation such as separation of the treatment.

EXAMPLES

In the Examples, all percents are by weight unless otherwise indicated. The non-amine contents in the following Examples and Comparative Examples were determined by the method described in AOCS official method Tw 1a-64, Percent Non-Amines in Fatty Amines and Diamines.

Example 1

Into a 1-liter flask was introduced 600 g of crude stearylamine having a non-amine content of 2.96%. The crude amine was heated to 80° C. with stirring in an air atmosphere, and 12.5 g of an aqueous sodium hydroxide solution (48% content) was added. This mixture was heated to 100° C., subsequently stirred for about 2 hours, and then purified by distillation to obtain stearylamine having a non-amine content of 0.26%. The distillation was conducted at 5 Torr until 240° C. The stearylamine obtained was visually examined for color (APHA; hereinafter referred to as color (1)). The stearylamine was placed in a flask, allowed to stand in a nitrogen atmosphere at 160° C. for 2 hours, and then visually examined again for color (APHA; hereinafter referred to as color (2)) so as to determine the color change. The results are shown in Table 1.

Into a 1-liter autoclave was introduced 400 g of the stearylamine obtained (total amine value: 211.9). After bubbling with nitrogen gas, the stearylamine was heated to 170° C., and 143 g of ethylene oxide was forced into the autoclave at a rate of 10 g/min at the constant temperature. The amine/ethylene oxide molar ratio was 1/2.15. After completion of the feeding, the mixture was aged for 30 minutes. The resultant ethylene oxide adduct of stearylamine (the number of moles of added ethylene oxide: 2.15) was discharged from the reactor.

The ethylene oxide adduct to stearylamine obtained was visually examined for color (APHA; hereinafter referred to as color (A)) and turbidity. About 60 g of the ethylene oxide adduct of stearylamine was placed in a glass tube, stored in a nitrogen atmosphere at 80° C. for 20 days, and then visually examined again for color (APHA; hereinafter referred to as color (B)) so as to determine the color change.

The results are shown in Table 1.

Comparative Example 1

Into a1-liter flask was introduced 600 g of crude stearylamine having a non-amine content of 2.96%. The crude amine was purified by distillation to obtain stearylamine having a non-amine content of 2.13%. The distillation was conducted at 5 Torr until 240° C.

The stearylamine obtained was visually examined for color (1) and color (2) in the same manner as in Example 1. The results are shown in Table 1.

Into a 1-liter autoclave was introduced 400 g of the stearylamine obtained (total amine value: 208.6). After bubbling with nitrogen gas, the stearylamine was heated to 170° C., and 141 g of ethylene oxide was forced into the autoclave at a rate of 10 g/min at the constant temperature. The amine/ethylene oxide molar ratio was 1/2.15. After completion of the feeding, the mixture was aged for 30 minutes. The resultant ethylene oxide adduct of stearylamine (the number of moles of added ethylene oxide: 2.15) was discharged from the reactor.

The ethylene oxide adduct of stearylamine obtained was visually examined for color (A), turbidity, and color (B) in the same manner as in Example 1.

The results are shown in Table 1.

Example 2

Into a 1-liter flask was introduced 600 g of crude laurylamine having a non-amine content of 1.98%. The crude amine was heated to 40° C. with stirring in an air atmosphere, and 3 g of potassium dihydrogen phosphate was added. This mixture was heated to 120° C., subsequently stirred for about 1 hour, and then purified by distillation to obtain laurylamine having anon-amine content of 0.12%. The distillation was conducted at 5 Torr until 210° C. The laurylamine obtained was visually examined for color (1) and color (2) in the same manner as in Example 1. The results are shown in Table 1.

Into a 1-liter autoclave was introduced 370 g of the laurylamine obtained (total amine value: 302.5). After bubbling with nitrogen gas, the laurylamine was heated to 180° C., and 190 g of ethylene oxide was forced into the autoclave at a rate of 10 g/min at the constant temperature. The amine/ethylene oxide molar ratio was 1/2.15. After completion of the feeding, the mixture was aged for 30 minutes. The resultant ethylene oxide adduct of laurylamine (the number of moles of added ethylene oxide: 2.15) was discharged from the reactor.

The ethylene oxide adduct of laurylamine obtained was visually examined for color (A), turbidity, and color (B) in the same manner as in Example 1.

The results are shown in Table 1.

Comparative Example 2

Into a 1-liter flask was introduced 600 g of crude laurylamine having a non-amine content of 1.98%. The crude amine was purified by distillation to obtain laurylamine having a non-amine content of 1.56%. The distillation was conducted at 5 Torr until 210° C. The laurylamine obtained was visually examined for color (1) and color (2) in the same manner as in Example 1. The results are shown in Table 1.

Into a 1-liter autoclave was introduced 370 g of the laurylamine obtained (total amine value: 296.3). After bubbling with nitrogen gas, the laurylamine was heated to 180° C., and 185 g of ethylene oxide was forced into the autoclave at a rate of 10 g/min at the constant temperature. The amine/ethylene oxide molar ratio was 1/2.15. After completion of the feeding, the mixture was aged for 30 minutes. The resultant ethylene oxide adduct of laurylamine (the number of moles of added ethylene oxide: 2.15) was discharged from the reactor.

The ethylene oxide adduct to laurylamine obtained was visually examined for color (A), turbidity, and color (B) in the same manner as in Example 1.

The results are shown in Table 1.

Example 3

Into a 1-liter flask was introduced 600 g of crude laurylamine having a non-amine content of 1.98%. The crude amine was heated to 40° C. with stirring in an air atmosphere, and 6 g of potassium hydrogen carbonate was added. This mixture was heated to 120° C. and then stirred for about 1 hour. Thereafter, the mixture was cooled to 80° C. and then filtered to obtain laurylamine having a non-amine content of 0.32%. The laurylamine obtained was visually examined for color (1) and color (2) in the same manner as in Example 1. The results are shown in Table 1.

Into a 1-liter autoclave was introduced 370 g of the laurylamine obtained (total amine value: 298.1). After bubbling with nitrogen gas, the laurylamine was heated to 180° C., and 187 g of ethylene oxide was forced into the autoclave at a rate of 10 g/min at the constant temperature. The amine/ethylene oxide molar ratio was 1/2.15. After completion of the feeding, the mixture was aged for 30 minutes. The resultant ethylene oxide adduct of laurylamine (the number of moles of added ethylene oxide: 2.15) was discharged from the reactor.

The ethylene oxide adduct of laurylamine obtained was visually examined for color (A) and color (B) in the same manner as in Example 1.

The results are shown in Table 1.

Comparative Example 3

Into a 1-liter autoclave was introduced 370 g of crude laurylamine having a non-amine content of 1.98% (total amine value: 292.9). After bubbling with nitrogen gas, the crude amine was heated to 180° C., and 183 g of ethylene oxide was forced into the autoclave at a rate of 10 g/min at the constant temperature. The amine/ethylene oxide molar ratio was 1/2.15. After completion of the feeding, the mixture was aged for 30 minutes. The resultant ethylene oxide adduct of laurylamine (the number of moles of added ethylene oxide: 2.15) was discharged from the reactor.

The feedstock crude laurylamine having a non-amine content of 1.98% was visually examined for color (1) and color (2) in the same manner as in Example 1.

The ethylene oxide adduct of laurylamine obtained was visually examined for color (A), turbidity, and color (B) in the same manner as in Example 1.

The results obtained for these are shown in Table 1.

Example 4

Into a1-liter flask was introduced 600 g of crude stearylamine having a non-amine content of 2.96%. The crude amine was heated to 80° C. with stirring in an air atmosphere, and 6 g of potassium phosphate was added. This mixture was heated to 100° C., subsequently stirred for about 2 hours, and then purified by distillation to obtain stearylamine having a non-amine content of 0.38%. The distillation was conducted at 5 Torr until 240° C. The stearylamine obtained was visually examined for color (1) and color (2) in the same manner as in Example 1. The results are shown in Table 1.

Into a 1-liter autoclave were introduced 300 g of the stearylamine obtained (total amine value: 210.2), an aqueous sodium hydride solution, and a 12% solution of a 50% aqueous sodium hydroxide solution. The amount of the aqueous sodium hydride solution introduced was 0.1 mol% based on the amine. After bubbling with nitrogen gas, the contents were heated to 160° C., and 205 g of ethylene oxide was forced into the autoclave at a rate of 10 g/min at the constant temperature. The amine/ethylene oxide molar ratio was 1/4.15. After completion of the feeding, the mixture was aged for 30 minutes. The obtained substance was discharged from the reactor and then purified by distillation to obtain the target ethylene oxide adduct of laurylamine (the number of moles of added ethylene oxide: 4.15).

The ethylene oxide adduct of stearylamine obtained was visually examined for color (A), turbidity, and color (B) in the same manner as in Example 1.

The results are shown in Table 1.

Comparative Example 4

Into a 1-liter flask was introduced 600 g of crude stearylamine having a non-amine content of 2.96%. The crude amine was purified by distillation to obtain stearylamine having a non-amine content of 2.13%. The distillation was conducted at 5 Torr until 240° C.

The stearylamine obtained was visually examined for color (1) and color (2) in the same manner as in Example 1. The results are shown in Table 1.

Into a 1-liter autoclave was introduced 300 g of the stearylamine obtained (total amine value: 208.2). After bubbling with nitrogen gas, the stearylamine was heated to 170° C., and 204 g of ethylene oxide was forced into the autoclave at a rate of 10 g/min at the constant temperature. The amine/ethylene oxide molar ratio was 1/4.15. After completion of the feeding, the mixture was aged for 30 minutes. The ethylene oxide adduct of stearylamine (the number of moles of added ethylene oxide: 4.15) was discharged from the reactor.

The ethylene oxide adduct of stearylamine obtained was visually examined for color (A), turbidity, and color (B) in the same manner as in Example 1.

The results are shown in Table 1.

TABLE 1

| | performances of feedstock amine | | | | performances of ethylene oxide | | |
| --- | --- | --- | --- | --- | --- | --- | --- |
| | base | non-amine content (%) | color (1) APHA | color (2) APHA | turbidity | color (A) APHA | color (B) APHA |
| example 1 | sodium hydroxide | 0.26 | <5 | 30 | clear | 30 | 40 |
| comp. ex. 1 | — | 2.13 | 10 | 100 | turbid | 100 | 300 |
| example 2 | potassium dihydrogen phosphate | 0.12 | <5 | 20 | clear | 20 | 40 |
| comp. ex. 2 | — | 1.56 | 5 | 80 | clear | 60 | 200 |

TABLE 1-continued

| | | performances of feedstock amine | | | performances of ethylene oxide | |
| --- | --- | --- | --- | --- | --- | --- |
| | base | non-amine content (%) | color (1) APHA | color (2) APHA | turbidity | color (A) APHA | color (B) APHA |
| example 3 | potassium hydrogen carbonate | 0.32 | <5 | 20 | clear | 30 | 50 |
| comp. ex. 3 | — | 1.98 | 10 | 90 | turbid | 30 | 100 |
| example 4 | potassium phosphate | 0.38 | <5 | 30 | clear | 150 | 200 |
| comp. ex. 4 | — | 2.13 | 10 | 100 | turbid | G2* | G4* | note) *:G is Gardner.

What is claimed is:

1. A process for producing an alkylene oxide adduct of a primary or secondary amine compound having an aliphatic, saturated or unsaturated, hydrocarbon radical having 8 to 22 carbon atoms, comprising:

adding a base or an aqueous solution thereof to the amine compound to form a mixture, heating the mixture to form a treated amine compound, optionally, separating the treated amine compound from the mixture, and reacting the treated amine compound with an alkylene oxide to form the alkylene oxide adduct of the amine compound.

2. The process as claimed in claim 1, wherein the base is selected from the group consisting of alkali metal or alkaline earth metal of hydroxides, carbonates, hydrogencarbonates, phosphates, hydrogenphosphates and dihydrogenphosphates.

3. The process as claimed in claim 1, wherein the base or an aqueous solution thereof is added in an amount such that the amount of pure base is 0.05 to 5 percent by weight of the amine compound.

4. The process as claimed in claim 1, wherein said heating the mixture is at a temperature of 60 to 180° C. for 0.1 to 3 hours.

5. The process as claimed in claim 1, wherein the treated amine compound is separated from the mixture by filtering and/or distilling it after the heating step.

6. The process as claimed in claim 1, wherein the amine compound is selected from the group consisting of octylamine, decylamine, laurylamine, stearylamine, behenylamine, oleylamine, dioctylamine, lilaurylamine, distearylamine, laurylstearylamine, and mixtures thereof, or is derived from an animal fat or a vegetable oil.

* * * * *